United States Patent [19]

Stockel

[11] Patent Number: 5,281,414
[45] Date of Patent: Jan. 25, 1994

[54] THREE-DIMENSIONAL WATER DISINFECTANTS

[76] Inventor: Richard F. Stockel, 475 Rolling Hills Rd., Bridgewater, N.J. 08807

[21] Appl. No.: 387,077

[22] Filed: Jul. 28, 1989

[51] Int. Cl.$^5$ .............................................. A61K 31/74
[52] U.S. Cl. ..................................... 424/78.1; 521/30; 521/32
[58] Field of Search ........................... 424/79; 521/30.4

[56] References Cited

U.S. PATENT DOCUMENTS

| | | | |
|---|---|---|---|
| 2,951,811 | 9/1960 | Lutz et al. | 424/79 |
| 3,817,860 | 6/1974 | Lambert et al. | 424/79 |
| 4,259,103 | 3/1981 | Malek et al. | 424/404 |
| 4,615,882 | 10/1986 | Stockel | 424/80 |
| 4,617,326 | 10/1986 | Bjornberg et al. | 424/443 |
| 4,645,757 | 7/1987 | Jerten et al. | 514/54 |

OTHER PUBLICATIONS

Chem. Abstracts vol. 99, entry 10874h.

Primary Examiner—Paul R. Michl
Assistant Examiner—Peter F. Kulkosky

[57] ABSTRACT

What is provided herein is a three-dimensional water disinfectant composition comprising the reaction product of a cross-linked, anti-microbial organosilicon quaternary ammonium salt and a macroporous cationic exchange resin. The cross-linked organosilicon quaternary ammonium salt suitably comprises about 2 to 60% by weight of the composition and the ion-exchange resin about 40 to 98% by weight of the composition. In a preferred form of the invention, the organosilicon compound constitutes about 20 to 40% by weight of the composition. Such compositions exhibit broad spectrum anti-bacteria activity including gram-negative activity, and are active algicidally in preventing the growth of algae in the water. The ion-exchange resin preferably is either a weak or strong cationic macroreticular ion-exchange resin. Methods of making such compositions also are described herein.

30 Claims, No Drawings

THREE-DIMENSIONAL WATER DISINFECTANTS

BACKGROUND OF THE INVENTION

1. Field of the Invention

This invention relates to anti- bacterial materials, and, more particularly, to three-dimensional solid systems suitable for disinfecting water and other liquids.

2. Description of the Prior Art

The preparation of demand-type broad-spectrum resin-polyiodide water disinfectants have been described in the prior art. Such triiodide-quaternary ammonium resin disinfectants have received primary consideration since the iodine is claimed to be tenaciously bound to the active sites of the resin and is released almost entirely on a demand action basis. U.S. Pat. Nos. 3,817,860; 3,923,665 and 4,238,477.

Prior to the present invention, however, these disinfectant systems were limited in their anti-bacterial activity by the available triiodide contained therein. Furthermore such systems are not known to exhibit any algicidal activity while in use in water purification systems.

The prior art in this field was concentrated mainly in two areas. U.S. Pat. Nos. 3,817,860 and 3,923,665 describes the use of commercially available strongly basic anion exchange resins whereby the chloride ion is exchanged for an $I_3^-$ ion. The triiodide modified ion exchange resin functions as a disinfectant for bacteria containing water in the form of the column of the cross-linked polymer beads through which the water is passed.

The acidic cation exchange resins which are operable are Rohm & Haas macroreticular Amberlyst ion exchange resins e.g. Amberlyst 15, Amberlyst XN-1010, Amberlite 200, Amberlite 252, Duolite C-26, Duolite C291, Amberlite IRC-50, Amberlite IRC-72 and Amberlite PP1. Other manufacturers offer similar products. These resins all have ion exchange groups and are supplied in the salt form, usually as the sodium or hydrogen, and as porous granular or beads of various mesh sizes.

Conventional ion exchange resins are essentially homogeneous crosslinked gels where the pore structure is the distance between polymeric chains. This type of molecular porosity is considered as microporous of microreticular. Macroreticular resins, in contrast, contain significant nongel porosity in addition to the normal gel porosity.

U.S. Pat. No. 4,238,477 describes a process to prepare resin-polyiodide disinfecting materials in a controlled and homogeneous manner. This process consists of converting the $X^-$ anion to the iodide form ($I^-$) followed by premeasuring an equivalent weight of iodine ($I_2$) needed to prepare the poly-iodide of choice, usually ($I_3^{31}$), dissolving the ($I_2$) in water, and continuously circulating the solution until the conversion is complete.

U.S. Pat. No. 4,420,590 expanded on this technology in that strongly basic anion-exchange resins with anion counter-ions were replaced with controlled relative proportion of iodide-bromide polyhalides.

This invention differs significantly from the prior art in that the germicidal activity is due entirely to the very strongly bound silane quaternary to either a carboxylate or sulfonate anionic site on the ion exchange resin. All other germicidal contact ion exchange resins depended on the presence of a halide, interhalide or intrahalide electrostatically bound to the resin as the activity site for the destruction of bacteria.

Silane quaternaries bonded to water-insoluble substrates has been shown to kill various type of bacteria. The first published report of this phenomenon was by Walters, Abbot and Isquith, Applied Microbiology, Feb., 1973, pgs. 253-256. Subsequent U.S. patents by these investigators, U.S. Pat. Nos. 3,730,701 and 3,794,736 disclosed suitable silane quaternaries operable as bound disinfecting contact germicides. A more recent U.S. Pat. No. 4,259,103, describes the overall procedure required to achieve such germicidal properties. More particularly, the process involves contacting a substrate, where ammonium, phosphonium or sulfonium cationic ions are present, with a silane quaternary having a hydrolyzable group attached to the silicon atom.

The prior art, however does not disclose or teach the preparation of an enhanced water disinfecting system by reacting a silane quaternary salt with a weak or strong cationic macroreticular ion exchange resin to form powerful and effective disinfecting systems.

Accordingly, it is an object of the present invention to provide a new and improved three-dimensional water contact disinfectant system which has a strong anti-bacterial effect with no leaching of any chemical substance.

Another object herein is to provide such a water disinfectant which has broad spectrum anti-bacterial activity including gram-positive, gram-negative and algicidal activity.

Still another object herein is to provide a three-dimensional water disinfectant which is a cross-linked organo-silicon quaternary ammonium salt attached to a macroreticular ion exchange resin.

Yet another object of the invention is to provide methods for preparing three dimensional water disinfecting system.

SUMMARY OF THE INVENTION

What is provided herein is a three-dimensional contact, non leaching water disinfectant composition comprising the reaction product of a cross-linked, antimicrobial organosilicon quarternary ammonium salt and macroreticular cationic ion-exchange resins. The cross-linked organosilicon quaternary ammonium salt suitable comprises about 2 to 60% of weight of the composition and the ion-exchange resin about 40 to 98% by weight of the composition. In a preferred form of the invention, the organosilicon compound constitutes about 20 to 40% by weight of the composition. Such compositions exhibit broad spectrum anti-bacterial activity including gram-negative activity, and are active algicidally in preventing the growth of algae in the water. The ion-exchange resin preferably is a weak or strong cationic macroreticular ion-exchange resin. Methods of making such compositions also are described herein.

The water disinfectant composition of the invention is made by cross-linking an organosilicon quaternary ammonium salt, preferably in weakly acidic medium and reacting the cross-linked compound with an appropriate ion-exchange resin.

The organosilicon quaternary ammonium salt suitably has a hydrolyzable group attached to the silicon atom which can react with the ion-exchange resin. Preferably such a group is a hydrocarbonoxy silane group, such as alkoxy or acyloxy which will provide reactive silanol groups in solution. Up to 3 such groups may be present in the molecule. A typical functional group is trimethoxy.

The ion-exchange resin suitably can be attracted electrostatically to the organosilicon quaternary or react therewith through an active hydrogen with the hydrolyzable group of the cross-linked silicon quaternary compound or intermingled by the polymeric form of the silane quat.

Another feature of the invention is the provision of an enhanced antibacterial product which is a reaction product of a cross-linked silane quaternary and a macroreticular cationic ion-exchange resin.

It should be emphasized that the silane quaternary ion-exchange resins of this invention are truly new and unique compositions. They have several outstanding features which set them apart from all previous disinfecting ion-exchange resin technologies.

The compositions of this invention are reaction products of weak or strong cationic macroreticular ion-exchange compounds. All previous disclosures were based on weakly or strongly anionic ion-exchange resins used were of the gel type cross-linked polymer systems.

This invention also teaches the preparation and use of a disinfecting ion-exchange system which is much less sensitive to the presence of electrolytes. Due to the common ion effect and/or swamping ion effect on the anion e.g. $I_3^-$, $Br^-$, $I^-$ etc. by another anion e.g. $Cl^-$, $Br^-$, $SO_4^{-2}$ etc., the microbiological efficacy of all prior art systems deteriorate. This invention is a significant improvement in that the drop-off in microbiological activity with increasing electrolyte concentration is minimized since neither of the above two mechanisms are operative.

DETAILED DESCRIPTION OF THE INVENTION

In accordance with the invention, there is provided herein a three-dimensional water disinfectant composition which shows a broad biocidal spectrum of activity as compared to the prior art.

Again it is worthwhile to reiterate the most important advancement of this invention, which allows disinfection of bacterial containing water without the concomitant leaching of halide ion. All other prior disclosures were plagued with this problem as illustrated in U.S. Pat. Nos. 3,316,173; 3,462,363; 3,817,590; 3,923,665; 4,076,622; 4,187,183; 4,238,477; 4,420,590; 4,594,361 and 4,594,392.

The anti-microbial organosilicon quaternary ammonium salt compounds used herein, and their preparation, are described in the literature, as for example, in U.S. Pat. Nos. 3,471,541; 3,560,385; 3,730,701; 3,817,739; 3,865,728; 4,005,028; 4,005,030; 4,394,378 and British Pat. 1,433,303. Particularly useful are those compounds described in U.S. Pat. Nos. 3,730,701, 3,817,739 and 4,394,378.

The essential characteristics of such compounds are anti-microbial activity, usually imparted by the presence of a long chain alkyl group on the quaternary nitrogen atom and a hydrolyzable group on the silicon atom which can react or be attracted to an ion-exchange resin. Generally the hydrolyzable group is a hydrolyzable hydrocarbonoxy group such as alkoxy or acyloxy, for reaction with an active hydrogen of the polymer. In water solution, alkoxy and acyloxy groups are hydrolyzed to hydroxyl groups, i.e., a silanol, for reaction with the polymer.

A useful class of anti-microbial organosilicon quaternary ammonium salts are described in U.S. Pat. No. 3,730,701 and has the general formula:

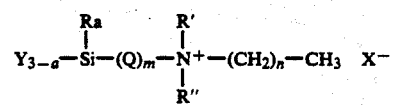

where

Y is a hydrolyzable radical, e.g. a hydrocarbonoxy group; e.g. alkoxy, or acyloxy;

R is a monovalent hydrocarbon group, e.g. lower alkyl or phenyl;

a is 0–2;

Q is a divalent hydrocarbon radical, e.g. alkylene or phenylene;

m is 1–20;

R' is alkyl C -C , aryl, alkaryl, or aralkyl;

R" is lower alkyl;

n is 9–17;

x is monovalent inorganic or organic radical or group selected from halogen; triiodide; acyloxy; or $YSO_4$- where Y is a monovalent hydrocarbon, hydrogen or —($CH_2$—)X —COOR''', where X is at least 2 and R''' is a monovalent hydrocarbon group fee of unsaturation.

Particularly useful compounds are those in which:

Y is alkoxy; e.g. methoxy;

R is lower alkyl; e.g. methyl;

m is 2–4; e.g. 3;

R' is lower alkyl or aralkyl; e.g. methyl or benzyl;

R" is lower alkyl;

n is 11–17, and

X is halogen or triiodide.

Typical organosilicon quaternary ammonium salts compounds for use herein include the following: 3-(trimethoxysilyl)propyloctadecyldimethyl ammonium chloride

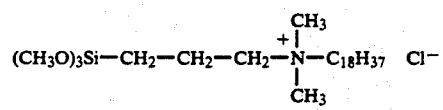

3-(triethoxysilyl)Propyloctadecyldimenthyl ammonium chloride

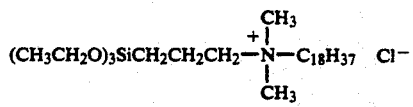

3-(methydimethoxysilyl)propyloctadecyldimethyl ammonium chloride

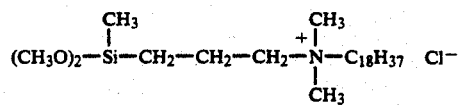

3-(phenyldimethoxysilyl)propyloctadecyldimethyl ammonium chloride

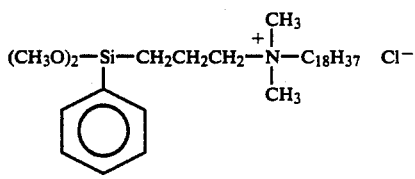

3-(dimethylmethoxysilyl)propyloctadecyldimethyl ammonium chloride

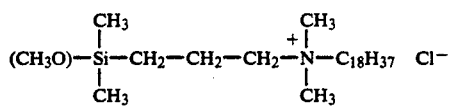

3-(diphenylmethoxysilyl)propyloctadecyldimethyl ammonium chloride

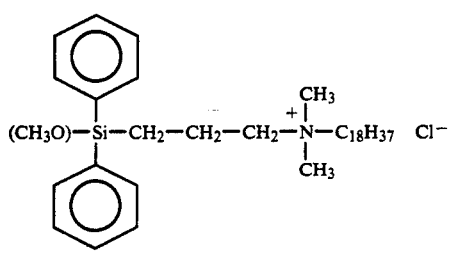

6-(methyldimethoxy)hexyloctadecyldimethyl ammonium chloride

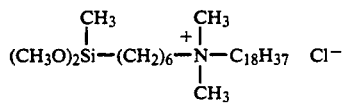

8-(methyldimethoxysilyl)octyloctadecyldimethyl ammonium chloride $$(CH_3O)_2-Si(CH_3)-(CH_2)_8-N^+(CH_3)(C_{18}H_{37})-CH_3 \quad Cl^-$$

12-(methyldimethoxysilyl)dodecyloctadecyldimethyl ammonium chloride $$(CH_3O)_2-Si(CH_3)-(CH_2)_{12}-N^+(CH_3)(C_{18}H_{37})-CH_3 \quad Cl^-$$

3-(methyldimethoxysilyl)propylmethyldidodecyl ammonium chloride $$(CH_3O)_2-Si(CH_3)-CH_2-CH_2-CH_2-N^+(CH_3)(C_{12}H_{25})-C_{12}H_{25} \quad Cl^-$$

3-(methyldimethoxysilyl)propylmethyldodecylbenzyl ammonium chloride

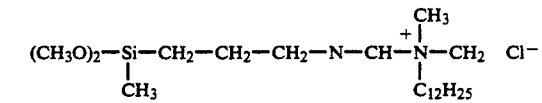

3-(methyldimethoxysilyl)propylbenzyldidodecyl ammonium chloride

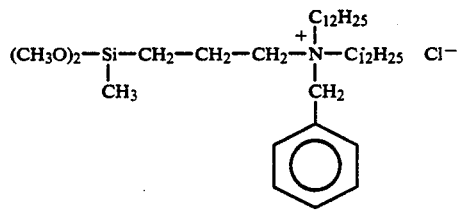

3-(trimethoxysilyl)propyloctadecyldimethyl ammonium bromide

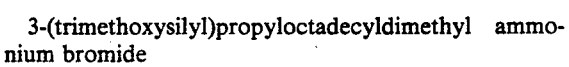

3-(trimethoxysilyl)propyloctadecyldimethyl ammonium triiodide

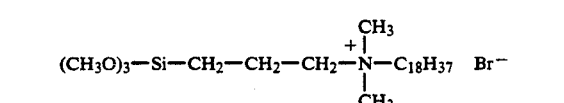

3-(trimethoxysilyl)propyloctadecyldimethyl ammonium acetate

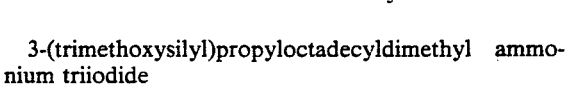

3-(trimethoxysilyl)propyloctadecyldimethyl ammonium sulfate

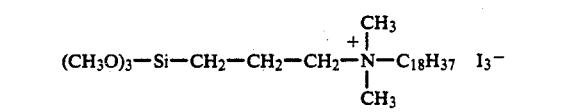

3-(methoxydimethylsilyl)propylmethyldidodecyl ammonium triiodide

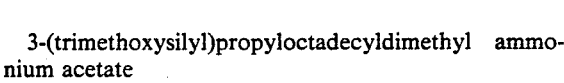

2-(trimethoxysilyl)ethyl p-benzyl dimethyoctadecyl ammonium chloride

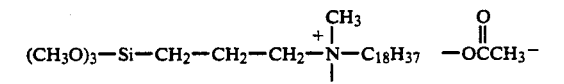

2-(trimethoxysilyl)ethyl-4-methylcyclohexyl dimethyl octadecyl ammonium chloride

EXAMPLE 2

Similarly, other commercial macroreticular resins were treated with silane quats to give the following compositions.

| Macroreticular Resin (wet) | Moisture Content of Resin % | Silane Quat (% by wt of Resin) |
|---|---|---|
| #2 Amberlite 200 ($SO_3^-$) | 49 | $(CH_3O)_2Si(CH_2)_3-\overset{+}{N}(CH_3)_2-C_{18}H_{37}$  $Cl^-$  (15) |
| #3 Duolite C-26 ($SO_3^-$) | 53 | $(CH_3O)_3Si(CH_2)_3-\overset{+}{N}(C_{10}H_{21})(CH_3)-C_{10}H_{21}$  $Cl^-$  (28) |
| #4 Amberlite IRC-72 ($COO^-$) | 73 | $(CH_3O)_3Si(CH_2)_3-\overset{+}{N}(CH_3)(CH_2\text{-Ph})-C_{12}H_{25}$  $Cl^-$  (38) |
| #5 Amberlite-252 ($COO^-$) | 48 | $(CH_3O)Si(CH_3)_2-(CH_2)_3-\overset{+}{N}(CH_3)_2-C_{18}H_{37}$  $Cl^-$  (25) |

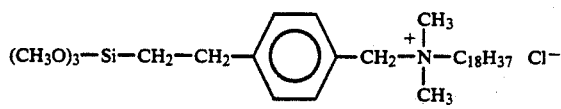

$(CH_3O)_3-Si-CH_2-CH_2-\text{[Ph]}-CH_2-\overset{+}{N}(CH_3)_2-C_{18}H_{37}\ Cl^-$

EXPERIMENTAL

The preparation of silane quats bound to cationic ion-exchange resins is carried out in a simple manner. The appropriate ion-exchange resin is stirred in an aqueous medium at room temperature which is acidified with acetic acid to a pH range of 5.5–6.5. Then the silane quat is added over a short period of time and the solution is stirred, usually for several hours until the silane quat is mostly reacted. Anywhere from 2 to 60 wt % of the silane quat can be reacted, however the preferred range is from 20 to 40 wt. %.

The resulting new anti-microbial composition is a tightly bound contact disinfectant ion-exchange resin, wherein the silane quat is both covalently and electrostatically bonded to the resin.

EXAMPLE I
Preparation of a Silane Quat Derivative of a Cationic Macroreticular Ion-Exchange Resin Thirty grams of wet Amberlite DP-1 was added to 75 ml of tap water. The pH of this mixture was about 6.0. To this mixture was added 10 grams of a 50 wt % methanolic solution of 3-(trimethoxysilyl) propyloctadecyldimethyl ammonium chloride. This caused the pH to become slightly basic, therefore, concentrated hydrochloric aqueous solution was added to give a slightly acidic pH of about 6.0+0.5. This mixture was stirred for about 15 hours, then filtered. The solid was thoroughly washed with water to remove any unreactive material.

EXAMPLE 3

Partial List of Cationic Macroreticular Amberlite[R]/Duolite[R] Ion-Exchange Resins

| Strong Acid Cation Exchanger | Weakly Acid Cation Exchanger |
|---|---|
| Amberlite 200 1.7 meqv/ml wet | Amberlite IRC-50 3.5 meqv/ml wet |
| Amberlite 200C 1.7 meqv/ml wet | Amberlite IRC-50S 3.5 meqv/ml wet |
| Amberlite 252 1.8 meqv/ml wet | Amberlite IRC-72 2.1 meqv/ml wet |
| Amberlite 252C 1.8 meqv/ml wet | Amberlite DP-1 2.5 meqv/ml wet |
| Duolite C-280 2.0 meqv/ml wet | Duolite C-464 3.0 meqv/ml wet |

EXAMPLE 4

The following table denotes the large differences between the pore characteristics of macroreticular and microreticular ion-exchange resins. This allows higher loading of the resin with the active silane quat concomitant with high flux rates.

| Material | Surface Area Sq. meters/g | Porosity % | Average Pore Diameter, A |
|---|---|---|---|
| Amberlyst 15 | 42.5 | 32 | 290 |
| Amberlite IR-120 | 0.1 | 1 | — |
| Amberlite IRA-400 | 0.1 | 1 | — |
| Amberlyst A-27 | 62.9 | 51 | 645 |

EXAMPLE 5

| Effect of various salt solutions on the disinfection of P. aeruginosa | | | |
|---|---|---|---|
| Resin/Silane Quat Complex | NaCl added Meg/ml | No. of microoganisms Added (volume ml) | Survived |
| Sample #1 | 0 | $4.6 \times 10\ 6(100)$ | <10 |

-continued

Effect of various salt solutions on the disinfection of *P. aeruginosa*

| Resin/Silane Quat Complex | NaCl added Meq/ml | No. of microoganisms Added (volume ml) | Survived |
|---|---|---|---|
| Sample #1 | 25 | $3.8 \times 10^6 (100)$ | <10 |
| Sample #1 | 50 | $3.8 \times 10^6 (100)$ | <10 |
| Sample #1 | 100 | $2.8 \times 10^6 (100)$ | <10 |

SAMPLE 6

The following table illustrates the efficacy of the silane quat/macroreticular complexes of this invention. About 10 g (dry wt) was added to a column and packed tightly by compressing while wet with water. Then about 250 ml of water containing E. coli was passed through the column and the eluent was tested for viable bacteria.

| | Viable counts of *e. coli* per ml | |
|---|---|---|
| Silane-quat/resin | Before passing | After passing |
| Sample #1 | $3.4 \times 10^5$ | 0 |
| Sample #2 | $2.6 \times 10^5$ | 0 |
| Sample #5 | $3.8 \times 10^5$ | 0 |

This experiment clearly demonstrates that strong and/or weak macroreticular ion-exchange resins can be useful for disinfecting bacterial contaminated water. Another difference is the use cationic exchange resins whereby all others use anionic exchange resins.

I claim:

1. A three-dimensional water disinfectant composition comprising the reaction product of (i) about 2 to 60 wt. % of an anti-microbial cross-linked organosilicon quaternary ammonium salt which includes a mono, di, or tri hydrolyzable silane group attached to the silicon atom, (ii) about 40 to 98 wt. % of strong or weak cationic macroreticular exchange resin reactive with said hydrolyzable silane group.

2. A water disinfectant composition according to claim 1 wherein said hydrolyzable silane group is a hydrocarbonoxy silane group.

3. A water disinfectant composition according to claim 1 wherein said exchange resin is in the form of beads.

4. A water disinfectant composition according to claim 1 wherein said reaction product comprises 20% to 40% of (i) and 60% to 80% of (ii).

5. A water disinfectant composition according to claim 2 wherein said hydrocarbonoxy silane group is an alkoxy silane group.

6. A water disinfectant composition according to claim 1 wherein said cross-linked organosilicon quaternary ammonium salt is formed from a compound which has the formula:

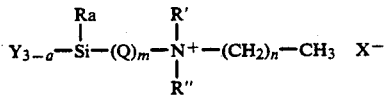

where
Y is a hydrolyzable radical, e.g. a hydrocarbonoxy group;
e.g. alkoxy, or acyloxy;
R is a monovalent hydrocarbon group, e.g. lower alkyl or phenyl;
a is 0–2;
Q is a divalent hydrocarbon radical, e.g. alkylene or phenylene;
m is 1–20;
R' is alkyl $C_1$-$C_{18}$, aryl, alkaryl, or aralkyl;
R" is lower alkyl;
n is 9–17;
x is monovalent inorganic or organic radical or group selected from halogen; triiodide; acyloxy; or $YSO_4^-$, where Y is a monovalent hydrocarbon, hydrogen, or $-(CH_2-)_x-COOR'''$, where x is at least 2 and R''' is a monovalent hydrocarbon group free of unsaturation.

7. A water disinfectant composition according to claim 6 wherein Y is an alkoxy or acyloxy group.

8. A water disinfectant composition according to claim 6 wherein Y is an alkoxy group.

9. A water disinfectant composition according to claim 6 wherein R is lower alkyl or phenyl.

10. A water disinfectant composition according to claim 6 wherein R is lower alkyl or phenyl.

11. A water disinfectant composition according to claim 6 wherein said organosilicon compound is 3-(trimethoxysilyl)propyloctadecyldimethyl ammonium chloride

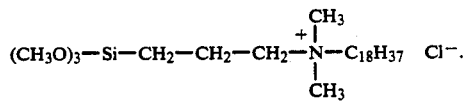

12. A water disinfectant composition according to claim 6 wherein said organosilicon compound is 3-(methyldimethoxysilyl)propyloctadecyldimethyl ammonium chloride

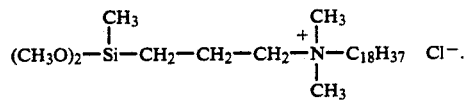

13. A water disinfectant composition according to claim 6 wherein said organosilicon compound is 3-(phenyldimethoxysilyl)propyloctadecyldimethyl ammonium chloride

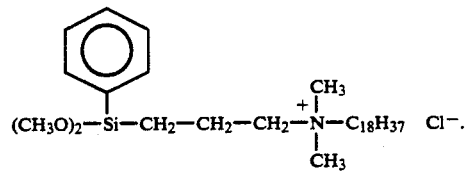

14. A water disinfectant composition according to claim 6 wherein said organosilicon compound is

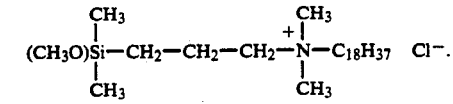

15. A water disinfectant composition according to claim 6 wherein said organosilicon compound is 3-(diphenylmethoxysilyl)propyloctadecyldimethyl ammonium chloride

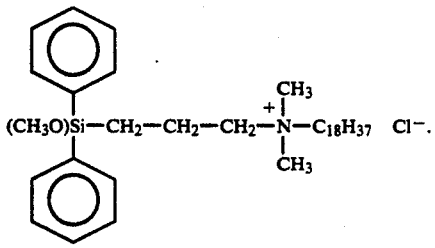

16. A water disinfectant composition according to claim 6 wherein said organosilicon compound is 6-(methyldimethoxy)hexyloctadecyldimethyl ammonium chloride

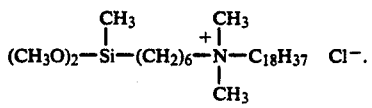

17. A water disinfectant composition according to claim 6 wherein said organosilicon compound is 8-(methyldimethoxysilyl)octyloctadecyldimethyl ammonium chloride

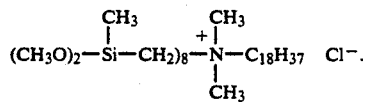

18. A water disinfectant composition according to claim 6 wherein said organosilicon compound is 12-(methyldimethoxysilyl)dodecyloctadecyldimethyl ammonium chloride

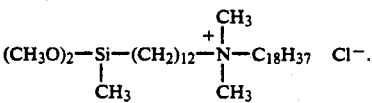

19. A water disinfectant composition according to claim 6 wherein said organosilicon compound is 3-(methyldimethoxysilyl)propylmethydidodecyl ammonium chloride

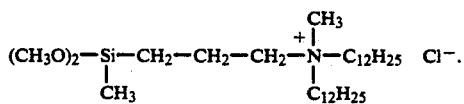

20. A water disinfectant composition according to claim 6 wherein said organosilicon compound is 3-(methyldimethoxysilyl)propylmethyldodecylbenzyl ammonium chloride

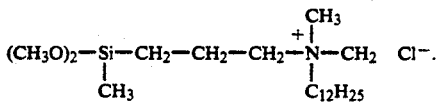

21. A water disinfectant composition according to cliam 6 wherein said organosilicon compound is 3-(methyldimethoxysilyl)propylbenzyldidodecyl ammonium chloride

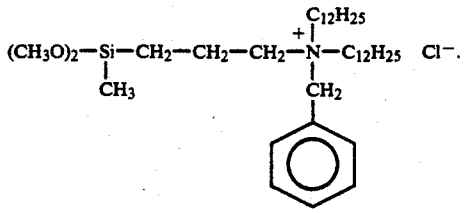

22. A water disinfectant composition according to claim 6 wherein said organosilicon compound is 3-(trimethoxysilyl)propyloctadecyldimethyl ammonium bromide

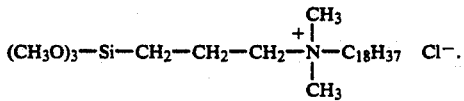

23. A water disinfectant composition according to claim 6 wherein said organosilicon compound is 3-(trimethoxysilyl)propyloctadecyldimethyl ammonium triiodide

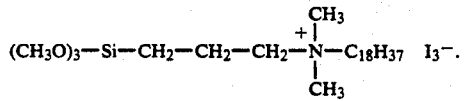

24. A water disinfectant composition according to claim 6 wherein said organosilicon compound is 3-(trimethoxysilyl)propyloctadecyldimethyl ammonium acetate

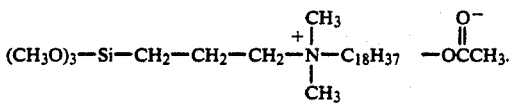

25. A water disinfectant composition according to claim 6 wherein said organosilicon compound is

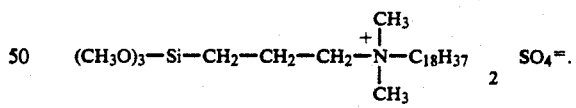

26. A water disinfectant composition according to claim 6 wherein said organosilicon compound is 3-(methoxydimethylsilyl)propylmethyldidodecyl ammonium triiodide

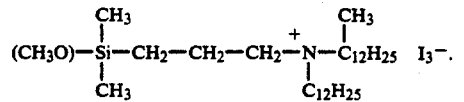

27. A water disinfectant composition according to claim 6 wherein said organosilicon compound is 2-(trimethoxysilyl)ethyl p-benzyl dimethyoctadecyl ammonium chloride

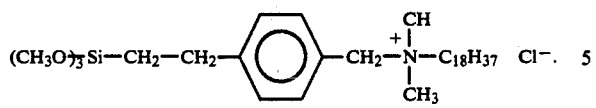

28. A water disinfectant composition according to claim 6 wherein said organosilicon compound is 2-(trimethoxysilyl)ethyl-4-methylcyclohexyl dimethyl octadecyl ammonium chloride

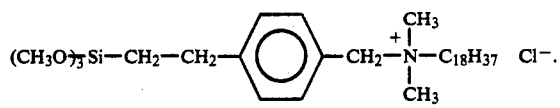

29. A water disinfectant system according to claim 1 in which said ion-exchange resin is a cationic macroreticular exchange resin.

30. Three-dimensional water reaction products according to claim 1 wherein said organosilicon quaternary ammonium salt has the formula:

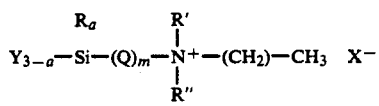

where
Y is a hydrolyzable radical;
R is a monovalent hydrocarbon group;
a is 0-2;
Q is a divalent hydrocarbon radical;
m is 1-11;
R' is alkyl $C_1$-$C_{18}$, aryl, alkaryl, or aralkyl;
R" is lower alkyl;
n is 9-17
X is monovalent inorganic or organic radical or group selected from halogen; triiodide; acyloxy; or $YSO_4^-$, where Y is a monovalent hydrocarbon, hydrogen, or —(CH) COOR''', where X is at least 3 and R''' is a monovalent hydrocarbon group free of unsaturation.

* * * * *